United States Patent
Jung et al.

(10) Patent No.: US 9,911,185 B2
(45) Date of Patent: Mar. 6, 2018

(54) METHOD OF GENERATING REFERENCE DATA FOR INSPECTING A CIRCUIT BOARD

(71) Applicant: KOH YOUNG TECHNOLOGY INC., Seoul (KR)

(72) Inventors: Seungwon Jung, Seoul (KR); Jongjin Choi, Gwangmyeong-si (KR); Heewook You, Seoul (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 0 days.

(21) Appl. No.: 15/021,349

(22) PCT Filed: Sep. 11, 2014

(86) PCT No.: PCT/KR2014/008473
§ 371 (c)(1),
(2) Date: Mar. 11, 2016

(87) PCT Pub. No.: WO2015/037918
PCT Pub. Date: Mar. 19, 2015

(65) Prior Publication Data
US 2016/0225129 A1    Aug. 4, 2016

(30) Foreign Application Priority Data

Sep. 12, 2013   (KR) ........................ 10-2013-0109909

(51) Int. Cl.
*G06K 9/00*   (2006.01)
*G06T 7/00*   (2017.01)
(Continued)

(52) U.S. Cl.
CPC ............ *G06T 7/001* (2013.01); *G01B 11/002* (2013.01); *G01N 21/93* (2013.01); *G01N 21/956* (2013.01);
(Continued)

(58) Field of Classification Search
CPC ........... G06T 7/001; G06T 2207/30141; G06T 2207/30148; G06T 7/0004; G06T 7/0006;
(Continued)

(56) References Cited

U.S. PATENT DOCUMENTS

| 4,443,756 | A | * | 4/1984 | Lightbody | ......... G01R 1/07392 324/750.25 |
| 4,528,500 | A | * | 7/1985 | Lightbody | ............. G01R 1/073 324/537 |

(Continued)

FOREIGN PATENT DOCUMENTS

| CN | 101852745 | 10/2010 |
| JP | 5-210712 | 8/1993 |

(Continued)

OTHER PUBLICATIONS

International Search Report for International Application No. PCT/KR2014/008473, dated Oct. 28, 2014.

*Primary Examiner* — Kanjibhai Patel
(74) *Attorney, Agent, or Firm* — Kile Park Reed & Houtteman PLLC

(57) ABSTRACT

The present invention relates to a method of generating reference data for inspecting a circuit board. The method comprises steps of scanning a bare circuit board to obtain image information of the bare circuit board, generating a compensation matrix using pad coordinate information extracted from the image information and pad coordinate information prestored in design data, and generating, by applying the compensation matrix to the image information, a reference data including coordinate information of a distinctive object. According to the method, inspection efficiency may optimized through quickly generating reference data without CAD information necessary for circuit board inspection.

10 Claims, 3 Drawing Sheets

(51) Int. Cl.
*G01N 21/93* (2006.01)
*G01N 21/956* (2006.01)
*G01B 11/00* (2006.01)

(52) U.S. Cl.
CPC . *G01N 21/95607* (2013.01); *G01N 21/95684* (2013.01); *G06T 7/0004* (2013.01); *G06T 7/0006* (2013.01); *G01N 2201/13* (2013.01); *G06T 2207/10016* (2013.01); *G06T 2207/30141* (2013.01); *G06T 2207/30148* (2013.01)

(58) Field of Classification Search
CPC . G01B 11/002; G01N 21/956; G01N 2201/13
USPC .......................................................... 382/147

See application file for complete search history.

(56) References Cited

U.S. PATENT DOCUMENTS

| | | | | |
|---|---|---|---|---|
| 4,583,857 | A | * | 4/1986 | Grammerstorff .... G01R 31/309 356/3.06 |
| 5,495,535 | A | * | 2/1996 | Smilansky ....... G01N 21/95607 348/E7.085 |
| 5,680,056 | A | * | 10/1997 | Ito ........................ G01R 31/309 324/501 |
| 2003/0130826 | A1 | | 7/2003 | Nguyen |
| 2010/0246931 | A1 | | 9/2010 | Kim et al. |
| 2012/0075643 | A1 | | 3/2012 | Yun et al. |

FOREIGN PATENT DOCUMENTS

| | | |
|---|---|---|
| JP | 10-221035 | 8/1998 |
| JP | 11-73513 | 3/1999 |
| JP | 2006-86432 | 3/2006 |
| JP | 2008-185514 | 8/2008 |
| JP | 2010-237210 | 10/2010 |
| JP | 2012-108131 | 6/2012 |
| JP | 2012-112961 | 6/2012 |
| KR | 10-2012-0032247 | 4/2012 |

* cited by examiner the present invention.

METHOD OF GENERATING REFERENCE DATA FOR INSPECTING A CIRCUIT BOARD

TECHNICAL FIELD

The present invention relates to a method of generating reference data for inspecting a circuit board, more specifically to a method of generating compensation matrix using pad coordinate information of an image information of a bare circuit board and pad coordinate information of design data and applying the compensation matrix to the image information to generate reference data for circuit board inspection.

BACKGROUND ART

In general, an electronic device comprises at least one of printed circuit board (PCB), and circuit patterns, connection pads, driving chip electrically connected to the connection pads and various other circuit elements are mounted on such printed circuit board.

A circuit board inspection apparatus is generally used for checking whether the above various circuit elements are correctly formed or arranged on the printed circuit board.

Generally, reference data is obtained for inspecting a printed circuit board. The reference data may be a theoretical plane image of a circuit board. The reference data may be obtained from CAD information which records a figure of the circuit board. The CAD information includes design standard information of the circuit board and generally includes information on arrangement of pads, circuit patterns, hole patterns and the like.

However, generating CAD information lowers efficiency of circuit board inspection because quite time is spent for generating CAD information for a circuit board and CAD information generating process shall be repeated if an error is occurred during CAD information generating process.

DISCLOSURE

Technical Problem

In order to solve the technical problem, the object of the present invention is to provide a method of generating reference data for circuit board inspection without generation of CAD information by generating a compensation matrix, using pad coordinate information of image information of a bare circuit board and pad coordinate information of prestored design data, and applying the compensation matrix to the image information of the bare circuit board to generate reference data including coordinate information of a distinctive object The object of the present invention is not limited by above, and other objects not mentioned above will be clearly understood by a person skilled in the art through the following descriptions.

Technical Solution

A method of generating reference data for circuit board inspection according to an embodiment of the present invention comprises steps of scanning a bare circuit board to obtain image information of the bare circuit board, generating a compensation matrix using pad coordinate information extracted from the image information and pad coordinate information of prestored design data, and generating, by applying the compensation matrix to the image information, a reference data including coordinate information of a distinctive object.

The step of generating a reference data may include steps of extracting the coordinate information of the distinctive object from the image information, and generating, by applying the compensation matrix to the extracted coordinate information of the distinctive object, the reference data.

The distinctive object may be at least one of hole pattern, circle pattern and a corner portion of a curved pattern, formed on the bare circuit board.

The reference data may be image information generated by applying the compensation matrix to the image information.

The image information may be a 2-dimensional image information of the bare circuit board.

A computer-executable program may be stored in a computer-readable storage medium.

Advantageous Effects

According to an embodiment of the present invention, a method of generating reference data and a method of inspecting a circuit board remarkably improves inspection efficiency because the method may generate reference data, which replaces CAD data, without generating CAD data of a circuit board for inspection so as to reduce time for generating CAD data.

MODE FOR INVENTION

The objects, the effects and the technical features of the present invention for obtaining them will be clearer with reference to the accompanying embodiments and drawings. In explaining the present invention, explanation of well-known function or structure, etc. that may get out of the point will be omitted. The terminology used herein is defined in consideration of a structure, a role, a function, etc. and may be changed according to an intention of a user or a practice.

However, the present invention may be embodied in many different forms and should not be construed as limited to the example embodiments set forth herein. Rather, these example embodiments are provided so that this disclosure will be thorough and complete, and will fully convey the scope of the present invention to those skilled in the art, and the present invention should be limited by claims. Therefore, the definition should be understood throughout the specification.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Hereinafter, with reference to the drawings, preferred embodiments of the present invention will be described in detail.

Figure 1:
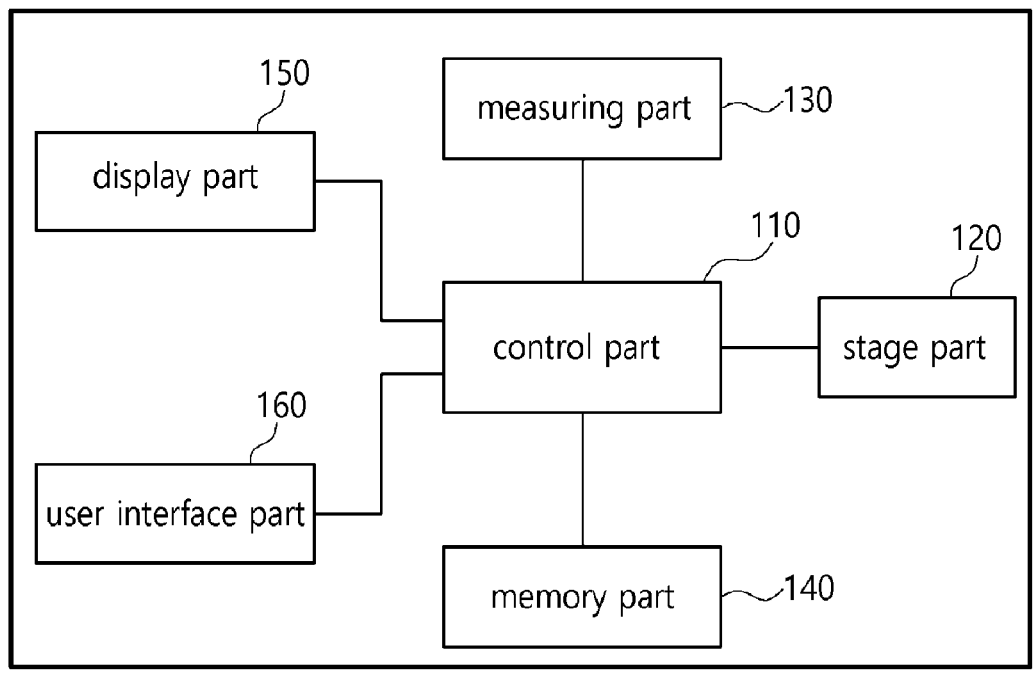
FIG. 1 is a block diagram illustrating a circuit board inspection apparatus performing a method of compensating inspected region according to an embodiment of the present invention.
Figure 2:
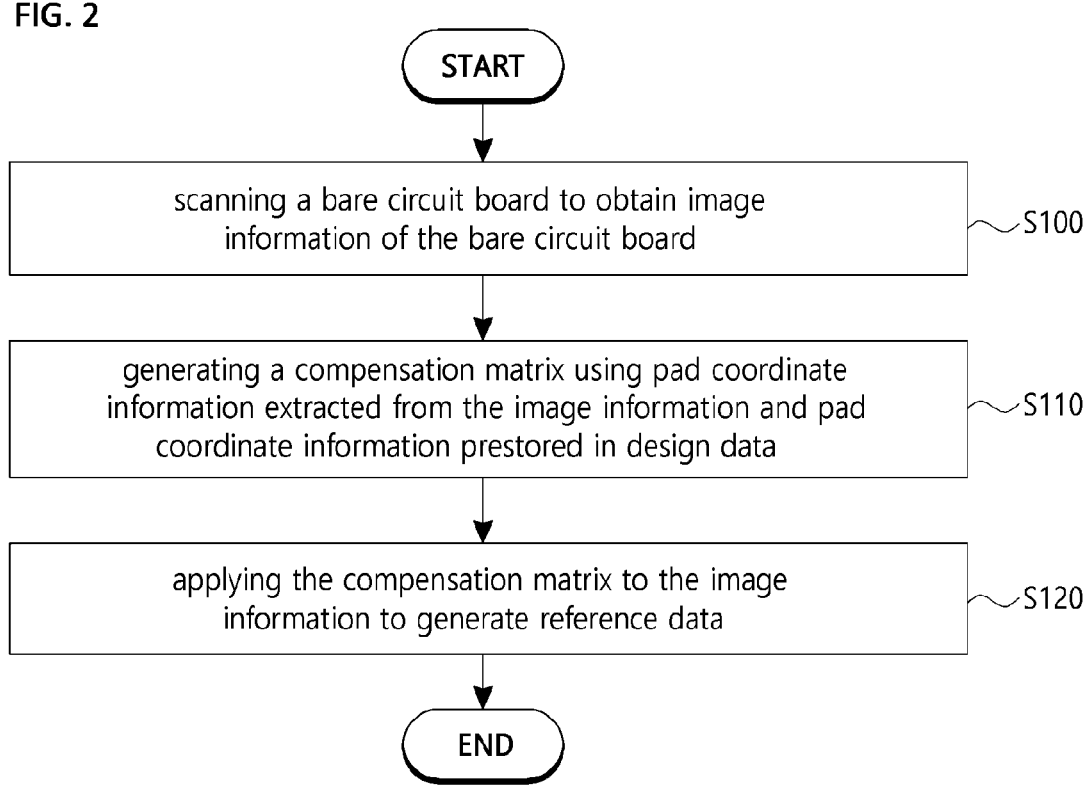
FIG. 2 is a flow chart illustrating a method of generating reference data for circuit board inspection according to an embodiment of the present invention.
Figure 3:
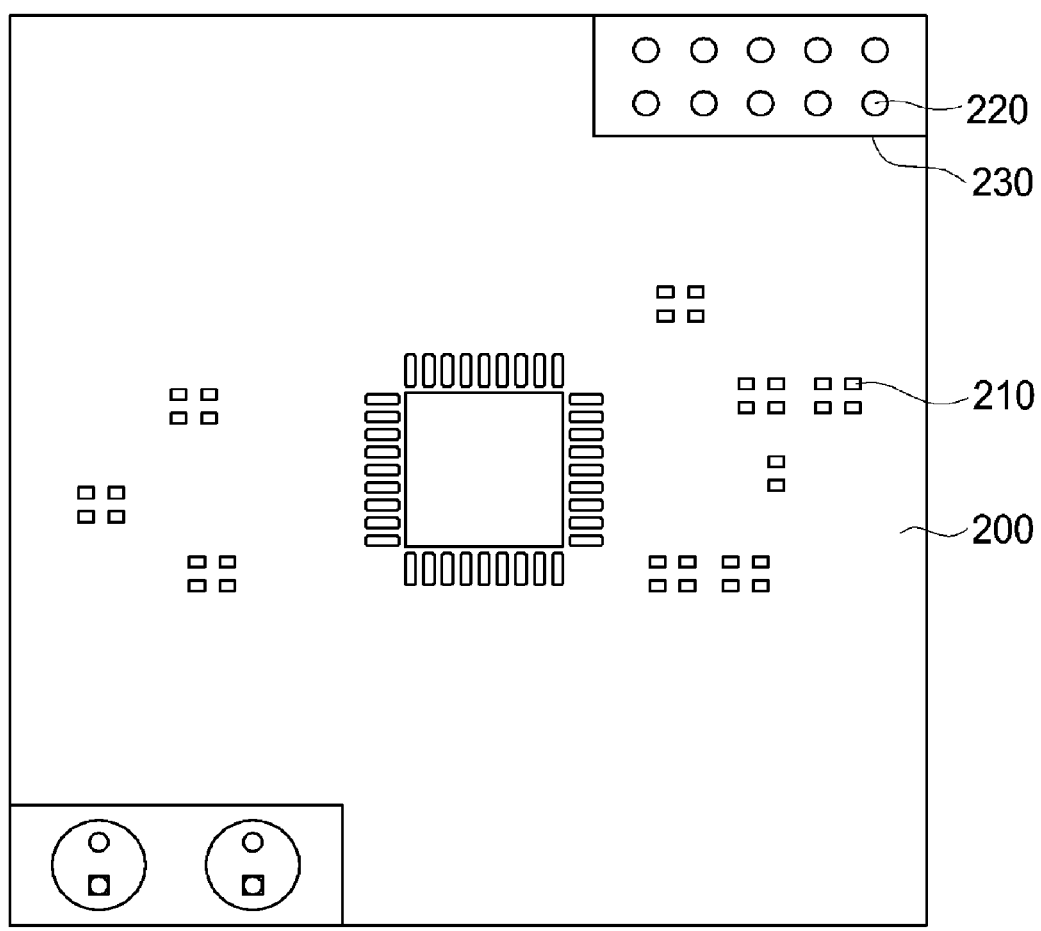
FIG. 3 is a plane view of a bare circuit board illustrating a method of generating reference data for circuit board inspection according to an embodiment of the present invention.

FIG. 1 is a block diagram illustrating a circuit board inspection apparatus performing a method of compensating inspected region according to an embodiment of the present invention, FIG. 2 is a flow chart illustrating a method of generating reference data for circuit board inspection according to an embodiment of the present invention, and FIG. 3 is a plane view of a bare circuit board illustrating a method of generating reference data for circuit board inspection according to an embodiment of the present invention.

Referring to FIG. 1, a circuit board inspection apparatus 100 may include a control part 110 controlling operation of the circuit board inspection apparatus 100 and processing for performing various functions, a stage part 120 loading and transferring a circuit board to be inspected, a measuring part 130 performing inspection for the circuit board loaded on the stage part 120, a memory part 140 storing data and program for operating the circuit board inspection apparatus 100, a display part 150 outputting operation status of the circuit board inspection apparatus and inspection results, and a user interface part 160 receiving a user command.

Referring FIG. 2 and FIG. 3, first, the measuring part 130 scans a bare circuit board 200 to obtain image information of the bare circuit board 200 S100.

A bare circuit board is a circuit board before soldering which means a circuit board where distinctive objects, such as pad areas 210 to be soldered, holes 220 and silks 230 not soldered.

The distinctive object may be at least one of hole pattern, circle pattern and a corner portion of a curved pattern, formed on the bare circuit board 200.

The image information may be a 2-dimensional image information of the bare circuit board 200.

Then, the control part 110 generates a compensation matrix using coordinate information of the pads 210 extracted from the image, and pad coordinate information prestored in design data S110.

At this time, the compensation matrix may be one of an Affine transformation matrix and projection transformation matrix.

Subsequently, the control part 110 applies the compensation matrix to the image information to generate reference data including coordinate information of the distinctive object S120.

The reference data may be generated in a form of coordinate information of the distinctive information or in a form of image information including coordinate information of the distinctive information.

For example, the control part 110 extracts coordinate information of the distinctive object from the image information, then applies the compensation matrix to the extracted coordinates of the distinctive object to generate reference data. In this case, the coordinate information itself is generated as reference data.

On the other hand, an image compensated by applying the compensation matrix to the image information of the bare circuit board may be generated as reference data.

The above described embodiment of the present invention does not generate CAD information but generate reference data including coordinate information of distinctive objects so as to optimize efficiency of inspection of circuit board.

Meanwhile, the reference data generated using the above described method of generating reference data for inspection of a circuit board may be used in inspection of a circuit board. In inspection of a circuit board, a distinctive object on the circuit board may be extracted and a compensation data may be generated using coordinate information of the distinctive object and coordinate information of the reference data for the distinctive object. Coordinate information of an inspection-target pad may be generated by applying the compensation matrix to coordinate information of the pad prestored in a design data. Then, inspection at a position according to the pad coordinate information may be performed.

The method of generating reference data for circuit board inspection may be implemented in a form of program instructions, which are executable by various computer means, and stored in a computer-readable storage medium. The computer-readable storage medium may include stand-alone or a combination of program instructions, data files and data structures. The program instructions stored in the computer-readable medium may be specially designed and constructed for the present invention, or well-known to person of ordinary skilled in computer software technology field. Examples of the computer-readable storage medium may include a magnetic medium, e.g., hard disk and floppy disk, an optical medium such as CD-ROM and DVD, a magneto-optical medium such as floptical disk, and a hardware device, i.e., ROM, RAM, and flash memory, specially constructed to store and execute program instructions. Examples of the program instructions include not only machine language code made by a compiler but also high level language code executable, using interpreter, etc., by a computer A method of compensating inspection area during circuit board inspection according to an embodiment may improve credibility of inspection by generating a compensation matrix using information of distinctive objects in neighboring inspection areas when validity of a compensation matrix generated using information of distinctive objects in a current inspection area is not credible.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

The invention claimed is:

1. A method of generating reference data for inspecting a circuit board, the method including:
   scanning a bare circuit board for the circuit board to obtain image information of the bare circuit board;
   generating a compensation matrix using pad coordinate information extracted from the image information and pad coordinate information prestored in design data; and
   generating, by applying the compensation matrix to the image information, a reference data including coordinate information of a distinctive object, wherein the reference data correspond to CAD information, and are prepared for a step of inspecting the circuit board.

2. The method of claim 1, wherein the generating a reference data includes:

extracting the coordinate information of the distinctive object from the image information;

generating, by applying the compensation matrix to the extracted coordinate information of the distinctive object, the reference data.

3. The method of claim 2, wherein the distinctive object includes at least one of hole pattern, circle pattern, and a corner portion of a curved pattern formed on the bare circuit board.

4. The method of claim 1, wherein the reference data is image information generated by applying the compensation matrix to the image information.

5. The method of claim 1, wherein the image information is a 2-dimensional image information of the bare circuit board.

6. A computer-readable storage medium storing computer-executable program for performing the method of claim 1.

7. A computer-readable storage medium storing computer-executable program for performing the method of claim 2.

8. A computer-readable storage medium storing computer-executable program for performing the method of claim 3.

9. A computer-readable storage medium storing computer-executable program for performing the method of claim 4.

10. A computer-readable storage medium storing computer-executable program for performing the method of claim 5.

* * * * *